(12) United States Patent
Chen et al.

(10) Patent No.: US 9,629,634 B2
(45) Date of Patent: Apr. 25, 2017

(54) INTRODUCER ACCESSORY

(75) Inventors: Wangdong Chen, Jiangsu (CN); Min Sun, Jiangsu (CN); Teng Shan, Jiangsu (CN); Yongwang Pei, Jiangsu (CN); Shuicheng Ding, Jiangsu (CN); Zongshun Wang, Jiangsu (CN); Kai Liu, Jiangsu (CN)

(73) Assignee: Suzhou Touchstone International Medical Science Co., Ltd., Suzhou (CN)

( * ) Notice: Subject to any disclaimer, the term of this patent is extended or adjusted under 35 U.S.C. 154(b) by 570 days.

(21) Appl. No.: 14/240,558

(22) PCT Filed: Aug. 23, 2012

(86) PCT No.: PCT/CN2012/080503
§ 371 (c)(1),
(2), (4) Date: Feb. 26, 2014

(87) PCT Pub. No.: WO2013/026400
PCT Pub. Date: Feb. 28, 2013

(65) Prior Publication Data
US 2014/0203064 A1    Jul. 24, 2014

(30) Foreign Application Priority Data

Aug. 24, 2011  (CN) ........................... 2011 1 0243513
Aug. 16, 2012  (CN) ........................... 2012 1 0291684
Aug. 16, 2012  (CN) ........................... 2012 1 0291706

(51) Int. Cl.
*A61B 17/068* (2006.01)
*A61B 17/115* (2006.01)
(Continued)

(52) U.S. Cl.
CPC ....... *A61B 17/1155* (2013.01); *A61B 17/1114* (2013.01); *A61B 17/32053* (2013.01);
(Continued)

(58) Field of Classification Search
CPC ............ A61B 17/07207; A61B 17/068; A61B 17/115; A61B 17/1155; A61B 17/0644;
(Continued)

(56) References Cited

U.S. PATENT DOCUMENTS 5,404,870 A * 4/1995 Brinkerhoff ........... A61B 17/00
227/175.1
2006/0229566 A1  10/2006 Hanagasaki
(Continued)

FOREIGN PATENT DOCUMENTS

CN       201676016 U     12/2010
CN       101991449 A      3/2011
(Continued)

OTHER PUBLICATIONS

Extended European Search Report issued on Jul. 17, 2015 for EP Application No. 12825929.8.

*Primary Examiner* — Michelle Lopez
(74) *Attorney, Agent, or Firm* — Fox Rothschild LLP

(57) ABSTRACT

An introducer accessory for being fitted with a circular stapler is disclosed, and pertains to the technical field of medical instrument. The introducer accessory at least comprises a sleeve portion sleeved around a distal end of the circular stapler and an introducing portion disposed at a distal end of the sleeve portion. And the introducing portion comprises a spiral member in a conical shape with a cavity and a traction member, the traction member extends in the cavity of spiral member to connect with the distal end of the spiral member such that when the traction member is pulled by an external force, the distal end of the spiral member is pulled out by the traction member through the cavity which causes the spiral member to be unwound internally and finally to form a strip body to withdraw through the circular (Continued)

stapler. Thus, the withdrawing process of introducer accessory can avoid injury to patient during surgery.

29 Claims, 16 Drawing Sheets

(51) Int. Cl.
  *A61B 17/34* (2006.01)
  *A61B 17/11* (2006.01)
  *A61B 17/3205* (2006.01)
  *A61B 90/00* (2016.01)

(52) U.S. Cl.
  CPC . *A61B 2017/3452* (2013.01); *A61B 2090/037* (2016.02); *F04C 2270/0421* (2013.01)

(58) Field of Classification Search
  CPC  A61B 2017/00473; A61B 2017/00336; A61B 17/064
  USPC .......................................... 227/175.1, 176.1
  See application file for complete search history.

(56) References Cited

U.S. PATENT DOCUMENTS

| | | | |
|---|---|---|---|
| 2007/0075117 A1 | 4/2007 | Milliman et al. | |
| 2008/0172087 A1 | 7/2008 | Fuchs et al. | |
| 2009/0204108 A1 | 8/2009 | Steffen | |
| 2010/0163598 A1 | 7/2010 | Belzer | |
| 2011/0036888 A1 | 2/2011 | Pribanic et al. | |
| 2011/0114697 A1* | 5/2011 | Baxter, III | ........... A61B 17/115 227/175.1 |
| 2011/0114698 A1 | 5/2011 | Baxter, III et al. | |

FOREIGN PATENT DOCUMENTS

| | | |
|---|---|---|
| CN | 102048569 A | 5/2011 |
| CN | 201855287 U | 6/2011 |
| CN | 202218890 U | 5/2012 |
| CN | 202313535 U | 7/2012 |
| CN | 202821483 U | 3/2013 |
| DE | 2928635 A1 | 2/1981 |
| JP | 2007503888 A | 3/2007 |
| JP | 2007523691 A | 8/2007 |
| WO | 2004032766 A2 | 4/2004 |
| WO | 2008089404 A2 | 7/2008 |

\* cited by examiner

Section A-A

INTRODUCER ACCESSORY

The present the U.S. National Phase of International Application Serial No. PCT//CN12/80503, filed Aug. 23, 2012, which claims priority to Chinese patent application No. 201110243513.1, entitled "introducer accessory", filed with the State intellectual Property Office of P.R.China on Aug. 24, 2011; Chinese patent application No. 201210291684.6, entitled "double spiral introducer", filed with State intellectual Property Office of P.R.China on Aug. 16, 2012; and Chinese patent application No. 201210291706.9, entitled"introducer", filed with the State Intellectual Property Office of P.R.China on Aug. 16, 2012. The contents of the foregoing applications are hereby incorporated by reference in their entireties.

TECHNICAL FIELD

The present, disclosure relates to a surgical auxiliary member for a circular stapler, in particular to an introducer accessory for the circular stapler.

BACKGROUND

The circular stapler is a surgical instrument widely used in stitching and cutting operations on tubular tissue. The circular stapler comprises a circular stapling head assembly and an actuating assembly. After placing two sections of tubular tissue to be joined together between an anvil and a staple cartridge of the stapling head assembly, a distance between the anvil and the staple cartridge is then adjusted to tightly clamp two sections, and next, the actuating member is operated to fire the staples and join the two sections of tissue together.

In actual operation procedures, when performing two operations, i.e. lower rectal operation and gastric bypass operation, the circular stapler is difficult to enter tubular tissue. In the lower rectal operation, a circular stapler with the diameter of 33 mm, which must be performed via anus, is adopted. As the anus is a muscular opening and has small diameter in normal state, large-diameter instrument is very difficult to be inserted into the anus. In the gastric bypass operation, a circular stapler with the diameter of 25 mm, which must be performed in small intestine, is adopted. As the small intestine is an alimentary canal of the human body, there are a lot of mucous membranes in the inner wall thereof. However, the circular stapler has large end surface and the surface is not smooth enough due to the structural features. Therefore, the mucous membranes tend to be damaged when the circular stapler is moved through the small intestine.

To solve the above problems, a plurality of auxiliary instruments sleeved around the periphery of a staple cartridge assembly of a circular stapler was developed in the prior art, which are disclosed in U.S. patent publication Nos. US2009/0204108 and US2011/0114698. By means of the auxiliary instrument, the staple cartridge assembly of the circular stapler can be introduced into the human body and moved through intestinal tracts; and the auxiliary instrument can be disengaged from the staple cartridge assembly after the circular stapler arrives at a predetermined surgical position, without any influence on the subsequent procedures of the circular stapler. The current auxiliary instruments can help surgeons to smoothly place a head of the stapler into the predetermined position, but they must be torn and pulled out by large force. Thereby, tissues tend to be damaged accidentally, and hence, the use experience is poor.

SUMMARY

The objective of the present disclosure is to solve the above technical problem and provide an introducer accessory which has a simple structure and is convenient to manipulate.

In order to achieve the objective, the present disclosure adopts the technical solutions as follows.

There is provided an introducer accessory for being fitted with a circular stapler, the circular stapler comprising an anvil assembly and a staple cartridge assembly, the staple cartridge assembly including a staple cylinder and a staple cartridge being mutually fixed, wherein lie introducer accessory at least comprises a sleeve portion sleeved around a distal end of the circular stapler and an introducing portion disposed at a distal end of the sleeve portion; a maximum outer diameter of the introducing portion is equal to a minimum outer diameter of the sleeve portion; the introducing portion is a spiral member, one end of a spiral wire of the spiral member is connected with a traction member and the other end is connected with the sleeve portion.

Preferably, outline of the introducing portion is conical with a hollow inner cavity.

Preferably, the sleeve portion is in a shape of a cylinder or a semicircular cylinder; and inner diameter of the sleeve portion is greater than outer diameter of the staple cylinder.

Preferably, the introducer accessory further comprises a flange for holding, which is disposed at a proximal end of the sleeve portion and configured to be spread out.

Preferably, a group of reinforcing ribs are perpendicularly disposed between adjacent spiral wires of the spiral member respectively.

Preferably, one end of the traction member is connected to a furthermost center of the spiral wire.

Preferably, the traction member runs through a through hole of the staple cylinder, and a pull ring is disposed at the other end of the traction member.

Preferably, the spiral member is configured to be consisted of two spiral wires which are alternately wound; first ends of the two spiral wires are connected with each other and second ends of the two spiral wires are connected with the sleeve portion.

Preferably, the traction member is hooked on a connected end portion of the two spiral wires.

There is also provided an introducer accessory for being fitted with a circular stapler, the circular stapler comprising an anvil assembly and a staple cartridge assembly, the staple cartridge assembly including a staple cylinder and a staple cartridge being mutually fixed, wherein the introducer accessory at least comprises a sleeve portion sleeved around a distal end of the circular stapler and an introducing portion disposed at a distal end of the sleeve portion; a maximum outer diameter of the introducing portion is equal to a minimum outer diameter of the sleeve portion; the introducing portion is a flexible U-shaped circuitous member with a U-shaped central cross-section formed by integral injection molding; the introducing portion has a proximal end and a distal end; and outer diameter of the distal end is less than or equal to outer diameter of the proximal end.

Preferably, the introducing portion and the sleeve portion are combined to form a flexible U-shaped circuitous member formed by integral injection molding such that when pulled by an external force, the flexible U-shaped circuitous member is disassembled and finally forms a strip body capable of being disengaged from the circular stapler.

Preferably, the sleeve portion is a thin wall sleeved around periphery of the staple cartridge.

Preferably, a clamp fixedly connected to the staple cartridge is disposed on the thin wall.

There is also provided an introducer accessory for being fitted with a circular stapler, the circular stapler comprising an anvil assembly and a staple cartridge assembly, the staple cartridge assembly including a staple cylinder and a staple cartridge being mutually fixed, and a trocar disposed in the staple cartridge, wherein the introducer accessory at least comprises a sleeve portion sleeved around a distal end of the circular stapler and an introducing portion disposed at a distal end of the sleeve portion; a maximum outer diameter of the introducing portion is equal to a minimum outer diameter of the sleeve portion; the introducing portion is a conical flexible plastic member with a cavity; the introducing portion has a proximal end and a distal end; the outer diameter of the introducing portion is gradually increased from the distal end to the proximal end; and when pulled by an external force, the plastic member is unwound spirally in a sequence from distal to proximal and finally forms a strip body capable of being disengaged from the circular stapler.

Preferably, the sleeve portion is a thin wall sleeved around periphery of the staple cartridge; and the introducing portion and the sleeve portion are combined to form a spiral flexible plastic member formed by integral injection molding.

Preferably, a central tube with inner diameter equal to outer diameter of a distal end of the trocar is protruded inwards from bottom of a distal end of a hollow inner cavity of the introducing portion.

Preferably, a traction hole is formed on a wall at a proximal end of the central tube which is one end of the whole flexible plastic member.

Preferably, at least one guide hole is formed on the staple cylinder of the circular stapler such that the introducing portion in the form of the strip body is disengaged from the circular stapler via the guide hole.

There is further provided an introducer accessory for being fitted with a circular stapler, the circular stapler comprising an anvil assembly and a staple cartridge assembly, the staple cartridge assembly including a staple cylinder and a staple cartridge being mutually fixed, and a trocar disposed in the staple cartridge, wherein the introducer accessory at least comprises a sleeve portion sleeved around a distal end of the circular stapler and an introducing portion disposed at a distal end of the sleeve portion; the maximum outer diameter of the introducing portion is equal to the minimum outer diameter of the sleeve portion; the introducing portion is a conical flexible plastic member with a cavity; the introducing portion includes a proximal end and a distal end, and outer diameter of the introducing portion is gradually increased from the distal end to the proximal end; a conical wall of the introducing portion includes a flexible strip and a second flexible strip which are attached tightly and arranged alternately and spirally; and when pulled by an external force, the conical wall is unwound spirally in a sequence from distal to proximal and finally forms a strip body which consists of the first flexible strip and the second flexible strip and can be disengaged from the circular stapler.

Preferably, the sleeve portion includes a first flexible strip and a second flexible strip which are attached tightly and arranged alternately and spirally; and the first flexible strip and the second flexible strip of the sleeve portion are respectively integrally formed with the first flexible strip and the second flexible strip of the introducing portion.

Preferably, wall thickness of the sleeve portion is less than that of the introducing portion.

Preferably, the first flexible ship is made of rigid material; the second flexible strips is made of soft materials; and the first flexible strip and the second flexible strip are mutually attached by bonding or over-molding.

Preferably, a traction member is disposed at a distal end of the first flexible strip.

Preferably, the traction member is an extension of the distal end of the first flexible strip, a free end of the traction member is extended to a proximal end of the circular stapler; or the traction member is a traction string fixed at the distal end of the first flexible strip.

There is additionally provided an introducer accessory for being fitted with a circular stapler, the circular stapler comprising an anvil assembly and a staple cartridge assembly, the staple cartridge assembly including a staple cylinder and a staple cartridge being mutually fixed, and a trocar disposed in the staple cartridge, wherein the introducer accessory at least comprises a sleeve portion sleeved at a distal end of the circular stapler and an introducing portion disposed at a distal end of the sleeve portion; a maximum outer diameter of the introducing portion is equal to a minimum outer diameter of the sleeve portion; the introducing portion is a conical flexible plastic member with a cavity, the introducing portion has a proximal end and a distal end, and outer diameter of the introducing portion is gradually increased from the distal end to the proximal end; a conical wall of the introducing portion includes an inner layer and an outer layer, wherein a first layer is a spiral body formed by the winding of a first flexible strip and a second layer is a second membrane layer covering on the first layer such that when pulled by an external force, the second membrane layer together with the first flexible strip are unwound spirally in a sequence from distal to proximal and finally forms a strip body capable of being disengaged from the circular stapler.

Preferably, the first flexible strip is tightly and spirally arranged; and the second membrane layer is only covering on outside or inside of the conical wall.

Preferably, the first flexible strip is spirally arranged; the second membrane layer is covering on outside or inside of the conical wall, and partial second membrane layer is extended into between spiral wires of the first flexible strip so that the first flexible strip and the second membrane layer can be attached tightly and arranged alternately and spirally.

Preferably, the sleeve portion is configured to the first flexible strip; and the first flexible strip of the sleeve portion and the first flexible strip of the introducing portion are integrally formed.

Preferably, the second membrane layer is covering on outside of the first flexible strips of the sleeve portion and the introducing portion.

Preferably, wall thickness of the sleeve portion is less than that of the introducing portion.

Preferably, the first flexible strip is made of rigid material; the second membrane layer is made of soft material; and the first flexible strips and the second membrane layer are mutually attached by bonding or over-molding.

Preferably, a traction member is disposed at distal end of the first flexible strip.

Preferably, the traction member is an extension of the distal end of the first flexible strip, a free end of the traction member is extended toward a proximal end of the circular stapler; or, the traction member is a traction string, fixed at the distal end of the first flexible strip.

The introducer accessory provided by the present disclosure has the advantages that: as a part or the whole introducer accessory can be pulled out from the circular stapler in one piece in the form of a strip, the operation is convenient; and as the introducer accessory can be directly sleeved around the outside of the circular stapler during surgery, no additional component is required to be assembled on the circular stapler.

BRIEF DESCRIPTION OF THE DRAWINGS

Further description will be given below to the technical proposals of the present disclosure with reference to the accompanying drawings.

Figure 1:
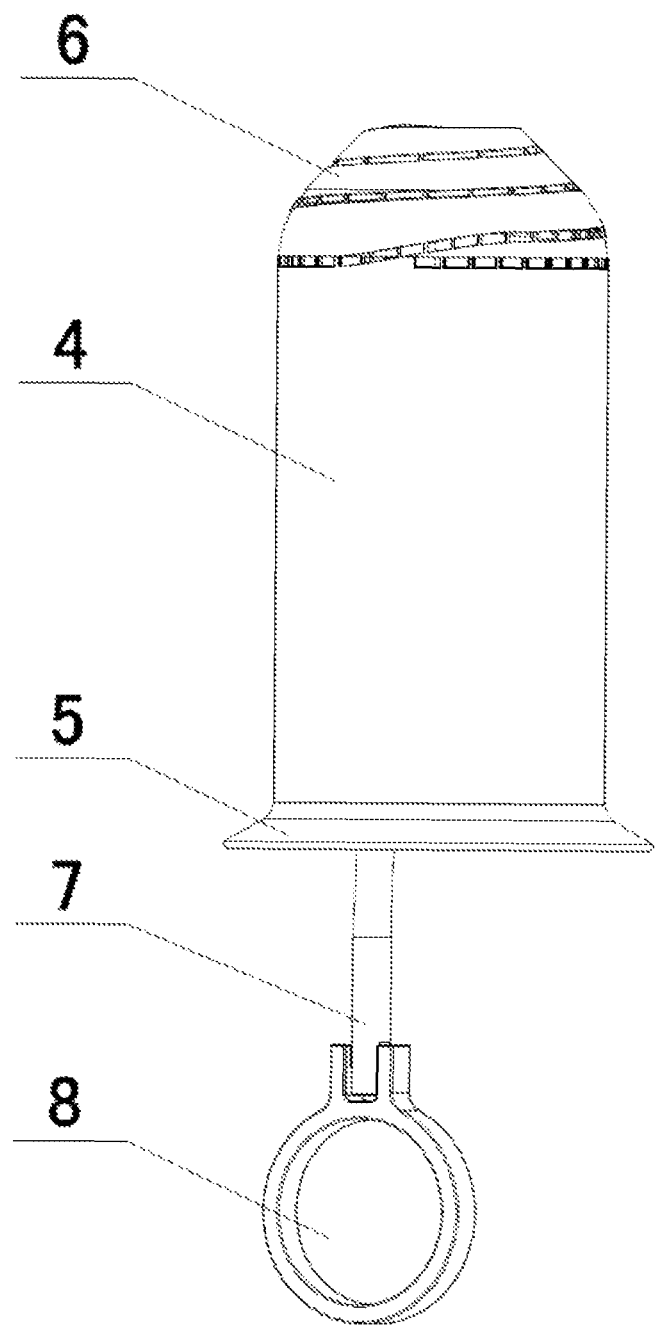
FIG. 1 is a schematic structural view of a first embodiment of the present disclosure.
Figure 2:
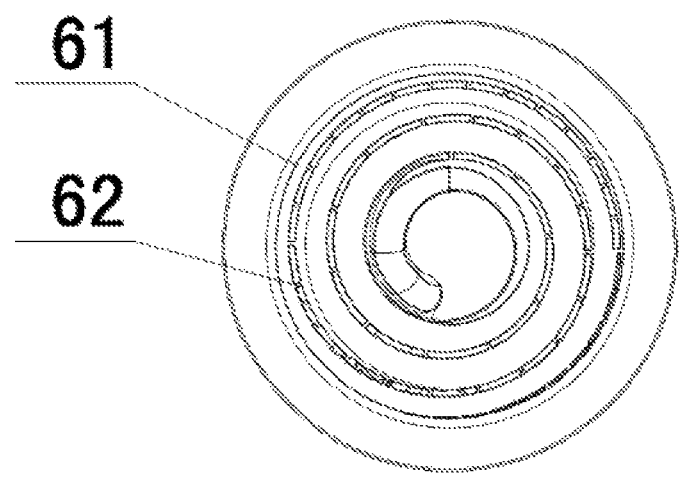
FIG. 2 is a top view of the first embodiment of the present disclosure.
Figure 3:
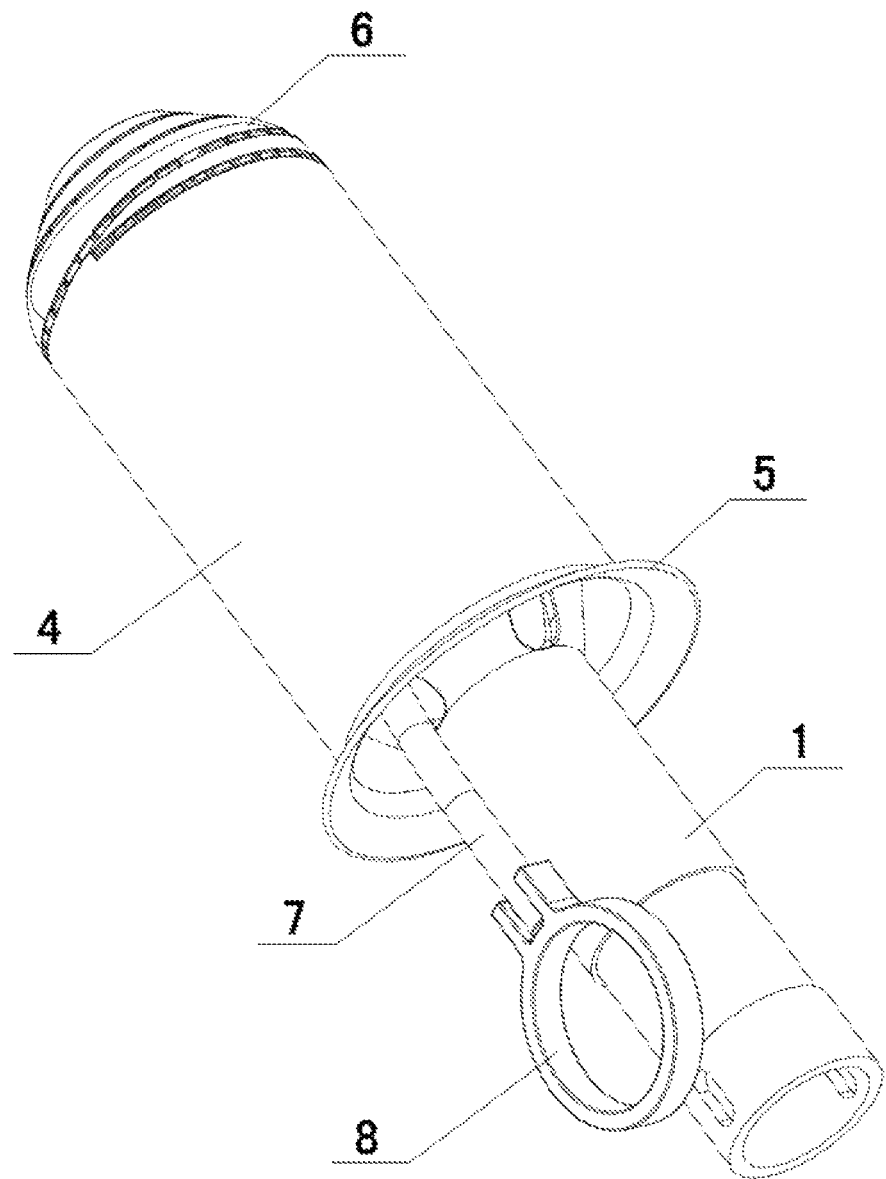
FIG. 3 is a schematic diagram illustrating the state when the first embodiment of the present disclosure is fitted with a circular stapler.
Figure 4:
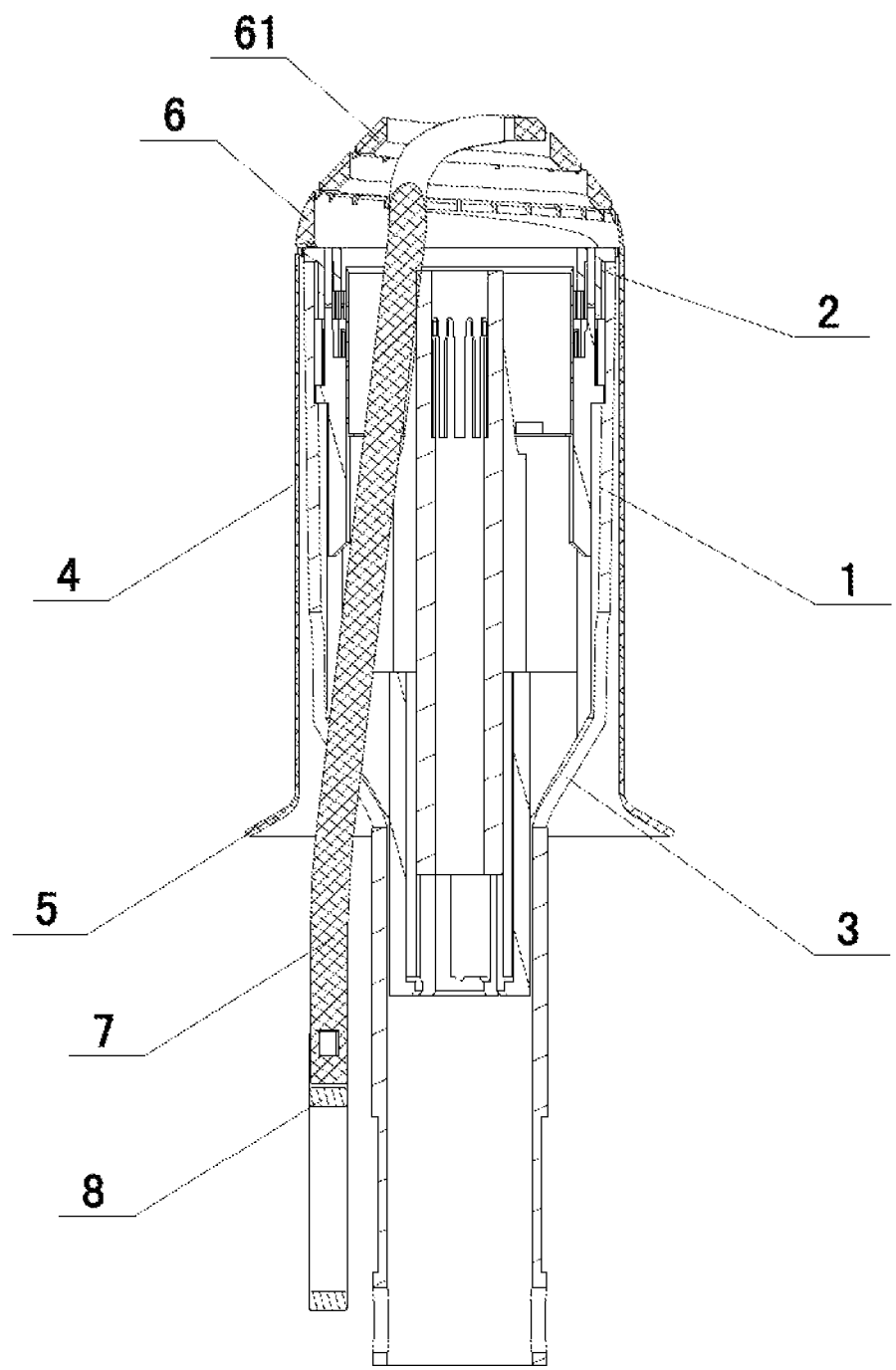
FIG. 4 is a sectional view of the first embodiment of the present disclosure.

Wherein:

| | | |
|---|---|---|
| 1 Staple cylinder | 2 Staple cartridge | 3 Through Hole |
| 4 Sleeve Portion | 5 Flange | 6 Introducing Portion |
| 61 Spiral wire | 62 Reinforcing Rib | 63 First Flexible Strip |
| 64 Second Flexible Strip | 65 Second Membrane Layer | 67 Tear Line |
| 7 Traction member | 8 Pull Ring | 15 Distal End |
| 17 Proximal End | 21 Central tube | 23 Traction hole |
| 25 Plane | 39 Clamp | |

DETAILED DESCRIPTION

The present disclosure discloses an auxiliary instrument for a circular stapler, in particular to an introducer accessory for introducing the circular stapler into the human body.

A circular stapler in the related art comprises an anvil assembly a staple cartridge assembly and a circular pipe fixed at a proximal end of the staple cartridge assembly, wherein the staple cartridge assembly includes a staple cylinder 1 and a staple cartridge 2 which are mutually fixed; and at least one through hole 3 is formed at a proximal end of the staple cylinder 1.

In the first embodiment as illustrated in FIGS. 1 to 4, the introducer accessory comprises: a sleeve portion 4 sleeved around a distal end of the circular stapler, an introducing portion 6 disposed at a distal end of the sleeve portion 4, and a flange 5 for holding which is disposed at a proximal end of the sleeve portion 4 and configured to be spread out.

The sleeve portion 4 is cylindrical with an inner diameter greater than the outer diameter of the staple cylinder. Thereby, the whole introducer accessory can be easily sleeved around the outside of the staple cylinder.

The outline of the introducing portion 6 is conical with 8 hollow inner cavity. The maximum outer diameter of the introducing portion 6 is equal to the minimum outer diameter of the sleeve portion. The introducing portion 6 is a spiral member, one end of a spiral wire 61 of the spiral member is connected with a traction member 7 and the other end is connected with the sleeve portion 4. A group of reinforcing ribs 62 are perpendicularly disposed between adjacent spiral wires 61 of the spiral member respectively. The connection between the introducing portion 6 and the sleeve portion 4 also depends on the reinforcing ribs 62. The reinforcing rib 62 is a plastic member with a narrow and thin end, similar to that on a beverage bottle cap, and can be easily pulled apart. After the reinforcing ribs 62 between the introducing portion 6 and the sleeve portion 4 are pulled apart, the introducing portion 6 and the sleeve portion 4 are disengaged from each other, without connection.

In the embodiment one end of the traction member 7 is connected to a furthermost center of the spiral wire 61. The traction member 7 runs through the through hole 3 of the staple cylinder. A pull ring 8 is disposed at the other end of the traction member 7.

In the operation process with the first embodiment, firstly, the introducer accessory is sleeved around the outside of the staple cartridge assembly, and the circular stapler is introduced into a surgical position in the human body via, a conical structure of the introducer accessory; then, the traction member is pulled via the pull ring, so that the spiral wires 61 connected to the traction member are applied by a force to pull apart the reinforcing ribs 62, and hence the spiral wires 61 of the whole introducing portion can be pulled out from the circular stapler in one piece in the form of a strip via the through hole 3. And next, the flange 5 is hand-held to pull the sleeve portion 4 sleeved around the outside of the staple cylinder toward the proximal end of the circular stapler, so that the sleeve portion 4 can be withdrawn from the human body. Therefore, the circular stapler can be used for surgery.

Figure 5:
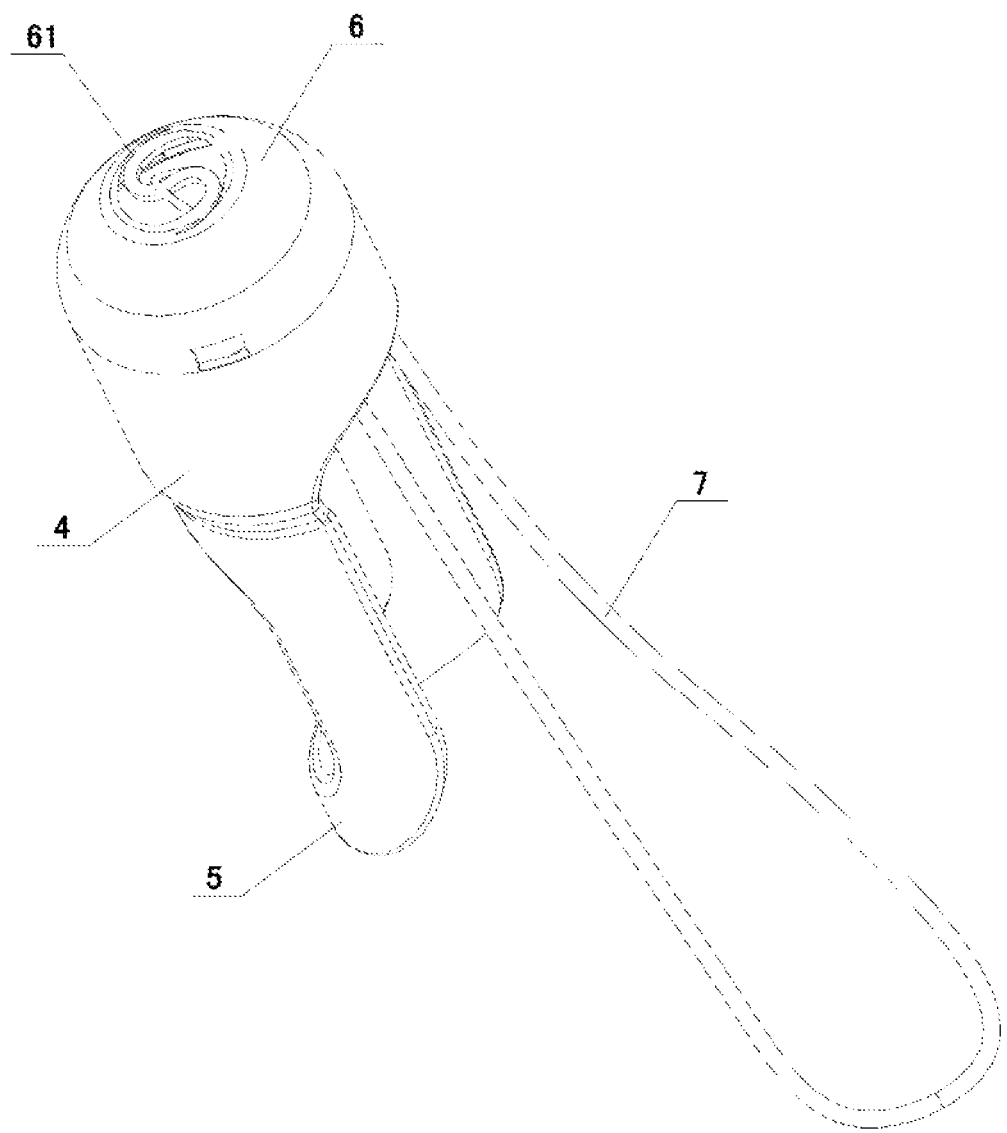
FIG. 5 is a schematic structural view of a second embodiment of the present disclosure.
Figure 6:
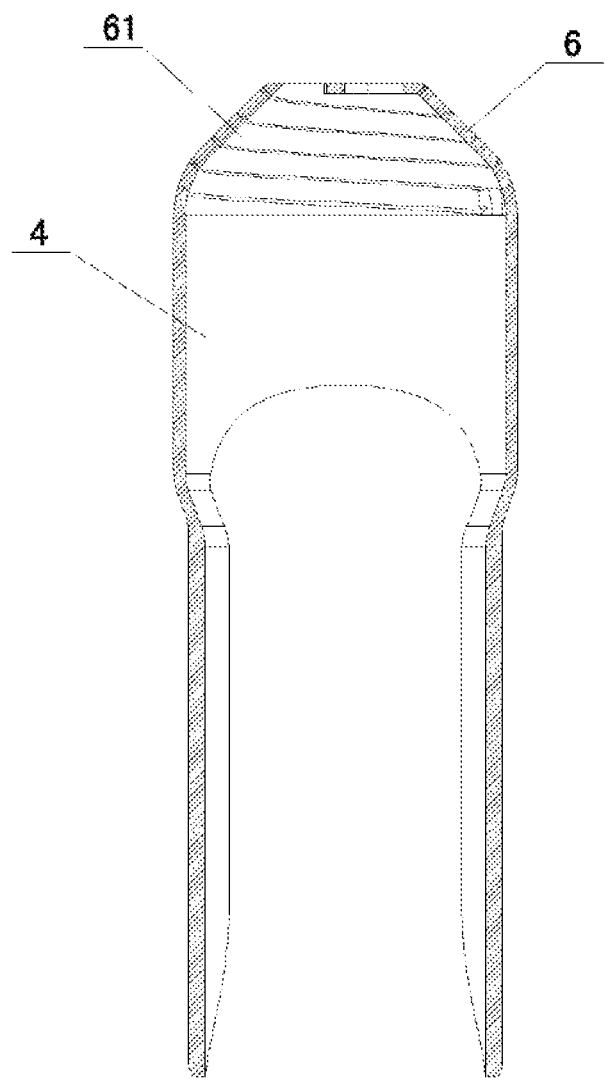
FIG. 6 is a sectional view of the second embodiment of the present disclosure.

FIGS. 5 and 6 illustrate the second embodiment of the present disclosure, in which the sleeve portion is in the shape of a semicircular cylinder. The main characteristic of the embodiment is that the spiral member is configured to be consisted of two spiral wires 61 alternately wound similar to the traditional mosquito coil incense. One end of one spiral wire 61 is connected with that of the other spiral wire 61 and the other ends of two spiral wires are connected with the sleeve portion via the reinforcing ribs 62. The traction member 7 is hooked on a connected end portion of the two spiral wires.

In the operation process with the second embodiment, firstly, the introducer accessory is sleeved around the outside of the staple cartridge assembly, and the circular stapler is introduced into a surgical position in the human body via a conical structure of the introducer accessory. Then, the traction member is pulled so that connecting ends of the two spiral wires are applied by a force to pull apart the reinforcing ribs 62, and hence the spiral wires 61 of the whole introducing portion are pulled out from the circular stapler in one piece in the form of a strip via the through hole 3. As the two spiral wires 61 are deformed and pulled out from the circular stapler at the same time, the operation time of the embodiment is faster than that of the first embodiment. And next, the flange 5 is hand-held to pull the sleeve portion 4 sleeved around the outside of the staple cylinder toward the proximal end of the circular stapler, so that the sleeve portion 4 can be withdrawn from the human body. Therefore, the circular stapler can be used for surgery.

Figure 7:
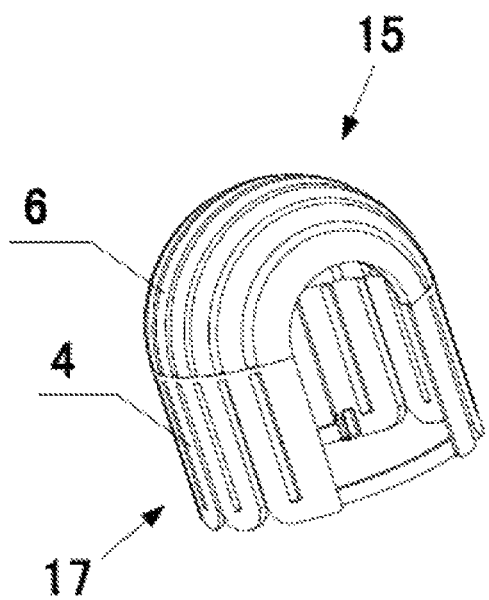
FIG. 7 is a schematic structural view of a third embodiment of the present disclosure.
Figure 8:
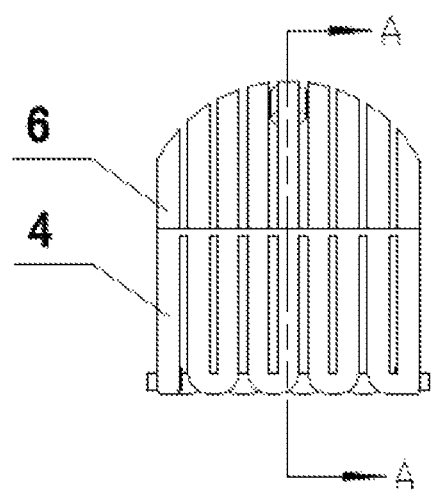
FIG. 8 is a front view of the third embodiment of the present disclosure.
Figure 9:
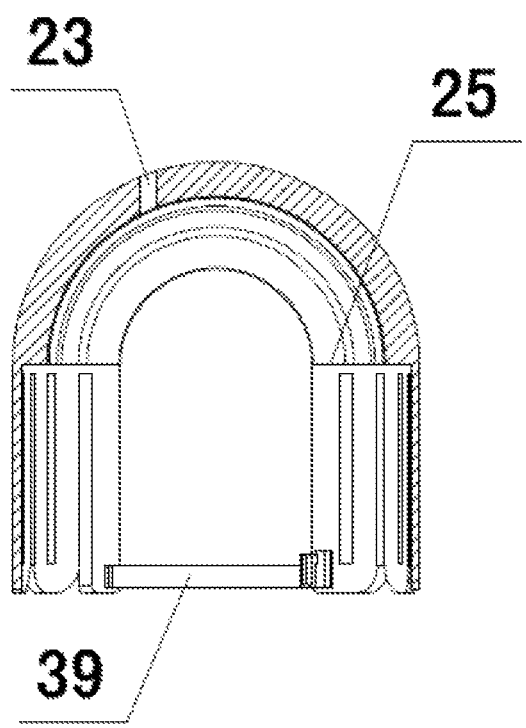
FIG. 9 is a sectional view of FIG. 8 along the A-A direction.

FIGS. 7 to 9 illustrate the third embodiment of the present disclosure. The characteristics of the embodiment is in that: the introducing portion 6 is a flexible U-shaped circuitous member formed by integral injection molding, a central cross-section of the U-shaped circuitous member is U-shaped; the introducing portion 6 has a proximal end 17 and a distal end 15; the outer diameter of the distal end 15 is less than or equal to the outer diameter of the proximal end 17; and the outer diameter of the proximal end 17 is equal to the outer diameter of the staple cartridge 3 or the staple cylinder 1. The main difference of the embodiment with the preceding embodiments is the winding shape of the "spiral wires" of the introducing portion.

Therefore, it is indicated that the shape of the "spiral wires" of the introducer accessory is not necessary. The spiral type, the U-shaped circuitous type as illustrated in the present disclosure, and other shapes may be adopted as long as a complete plastic strip encircles. That is, the U-shaped circuitous plastic member in the third embodiment may also be applied in the first embodiment.

In the embodiment, a plane for being attached to a staple cartridge surface is formed at the proximal end 17 of the introducing portion, and the sleeve portion 4 is a thin wall sleeved around the periphery of the staple cartridge. The thin wall and the introducing portion 6 are configured to be the flexible U-shaped circuitous member by integral injection molding. A clamp 39 fixedly connected to the staple cartridge is disposed on the thin wall.

As the operation method is roughly the same as that of the first embodiment, no further description will be given below.

Figure 10:
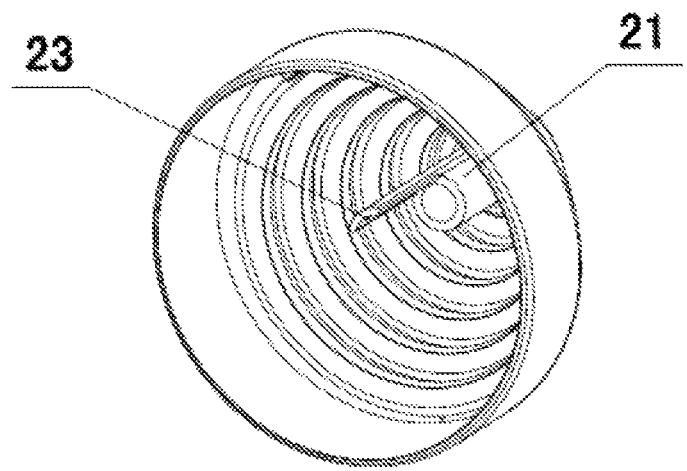
FIG. 10 is a schematic structural view of a fourth embodiment of the present disclosure.
Figure 11:
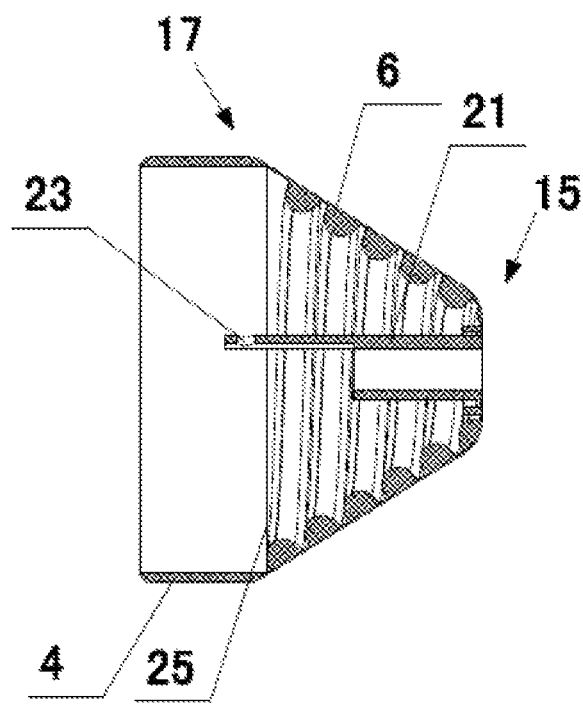
FIG. 11 is a sectional view of the fourth embodiment of the present disclosure.

FIGS. 10 and 11 illustrate the fourth embodiment of the present disclosure. The embodiment is similar to the first embodiment in that: the introducing portion 6 is a spiral flexible plastic member formed by integral winding, that is, the introducing portion 6 is a spiral member, like a spring, formed by the integral winding of a flexible plastic member. The introducing portion 6 is just a section of "spring wire".

In the embodiment, a central tube 21 is protruded inwards at the bottom of a distal end 15 of a hollow inner cavity of the introducing portion 6; and the inner diameter of the central tube 21 is equal to the outer diameter of a distal end of the trocar. Therefore, in the initial state, the introducer accessory may be sleeved around the trocar by the central tube 21, so that the introducer accessory can be fitted with the circular stapler.

A traction hole 23 is formed on a wall at a proximal end of the central tube 21; and the proximal end of the central tube is one end of the whole flexible plastic member, namely one end of the "spring wire".

A plane 25 to be attached to the staple cartridge surface 5 is formed at the proximal end of the introducing portion 6, the sleeve portion 4 is a thin wall sleeved around the periphery of the staple cartridge. The thin wall and the introducing portion 6 are configured to be a spiral flexible plastic member formed by integral injection molding.

In the operation process with the embodiment, firstly, the introducer accessory is sleeved around a distal end of the staple cartridge assembly; then, the circular stapler is introduced into the human body; and next, the traction string connected to the traction hole is pulled so that the introducer accessory can be integrally pulled out from the circular stapler in one piece in the form of a strip, which is similar to the state of pulling the "spring wire" into a straight wire.

In the above embodiments, the introducing portion is pulled out from the inside of the stapler, namely at least one guide hole is formed on the staple cylinder of the circular stapler. The introducing portion is unwound in the form of a strip and disengaged from the circular stapler via the guide holes. Certainly, the above embodiments may also be changed to be pulled out from the outside of the stapler, provided that a connecting position of the traction member on the introducer accessory is changed.

Figure 12:
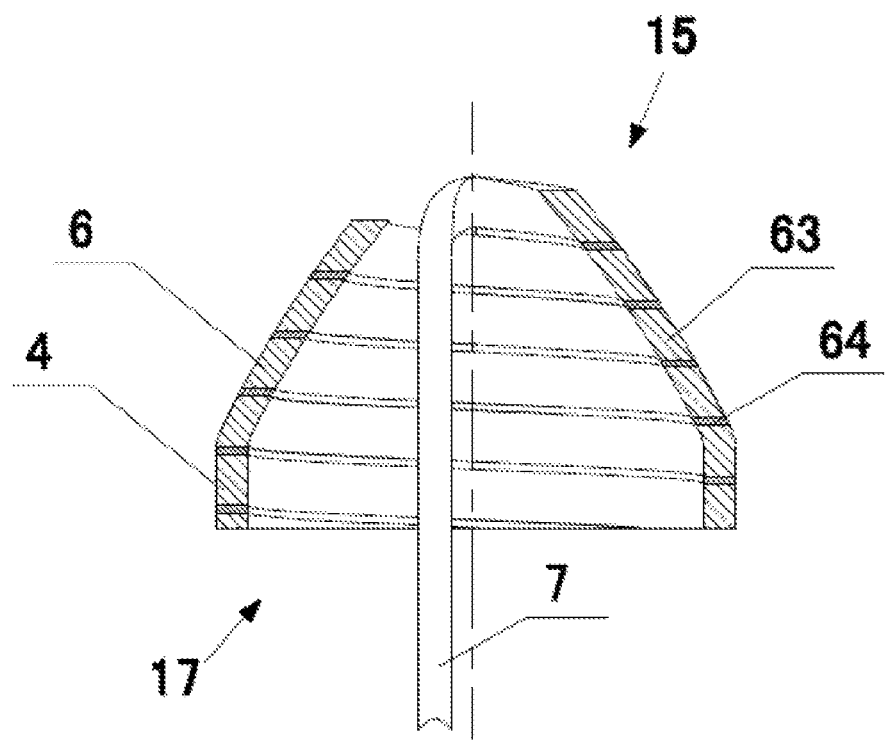
FIG. 12 is a schematic structural view of a fifth embodiment of the present disclosure.
Figure 13:
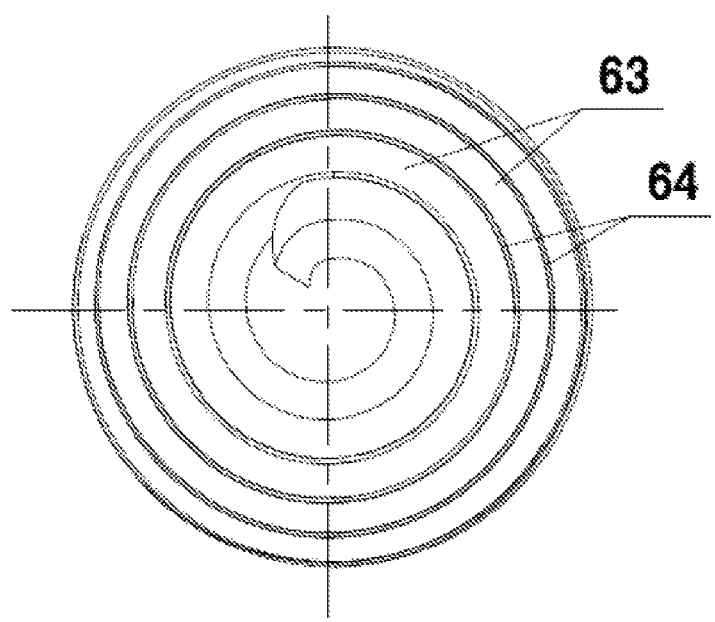
FIG. 13 is a top view of the fifth embodiment of the present disclosure.

FIGS. 12 and 13 illustrate the fifth embodiment of the present disclosure. The introducer accessory of the embodiment is a flexible plastic member in a conical shape with a hollow cavity. As the flexible plastic member wound to be the introducer accessory may be made of rubber or other plastics, the "spring wire" of the introducer accessory may be made to have different thicknesses depending on different level process, resulting in the inner cavities of the introducer with different dimensions. The introducing portion 6 of the introducer accessory has a proximal end 17 and a distal end 15, the outer diameter of the introducing portion 6 is gradually increased from the distal end 15 to the proximal end 17, and the diameter of an inner wall of the proximal end 17 is greater than or equal to the maximum outer diameter of the staple cylinder 1. Therefore, when the introducer accessory is fitted with the circular stapler, the introducer accessory may be sleeved around the periphery of the staple cylinder 1.

The characteristics of the embodiment are as follows. A conical wall of the introducing portion 6 includes a first flexible strip 63 and a second flexible strip 64 which are parallel to each other and wound to form a spiral body; and the first flexible strip 63 and the second flexible strip 64 are attached with each other and alternately and spirally arranged. The first flexible strip 63 is made of relatively rigid material, thereby with higher strength and higher hardness; and the second flexible strip 64 is made of relatively soft material, thereby with lower strength and being easily torn. There are various types of medical plastics, e.g. polyvinylchloride (PVC), polyethylene (PE), polypropylene (PP), polyethylene terephthalate (PET), polyurethane (PU) polystyrene (PS), polycarbonate (PC) and polytetrafluoroethylene (PTEE), and the only condition for selecting the material is to satisfy the above strength. Moreover, the first flexible strip 63 and the second flexible strip 64 are mutually attached by bonding or over-molding.

The sleeve portion 4 includes a first flexible strip 63 and a second flexible strip 64 which are alternately and spirally arranged and tightly attached with each other. The first flexible strip and the second flexible strip of the sleeve portion 4 are respectively integrally formed with the first flexible strip and the second flexible strip of the introducing portion 6.

As the first flexible strip 63 and the second flexible strip 64 are mutually and tightly wound, the conical wall of the whole introducing portion 6 has relative high strength and hence cannot be collapsed when the circular stapler is introduced into the body of a patient. Moreover, as the first flexible strip 63 and the second flexible strip 64 are mutually and tightly wound, the outside of the conical wall of the whole introducing portion 6 is relatively smooth, so that the outer wall cannot scratch the tissue when the circular stapler is introduced into the body of the patient, and thereby with much better effect than that of single spiral flexible strip.

A traction member 7 is also disposed at a distal end of the first flexible strip 63. The traction member 7 is an extension of the distal end of the first flexible strip 63, and a free end of the traction member 7 is extended toward the proximal end of the circular stapler. Alternatively, the traction member 7 may also be a traction string fixed at the distal end of the first flexible strip 63 as long as the pulling function can be achieved. Moreover, at least one guide hole is formed on the staple cylinder of the circular stapler and the traction member 7 in the initial state runs through the guide hole.

In the operation process of the embodiment, firstly, the introducer accessory of the preferred embodiment is sleeved around a distal end of the staple cartridge assembly; then, the circular stapler is introduced into the human body, and at this moment, the free end of the traction member 7 runs through the guide hole and is exposed out of the body of a patient; and next, the traction member 7 is pulled so that the first flexible strip 63 is unwound spirally in a sequence from distal to proximal and finally forms a strip body which consists of the first flexible strip and the second flexible strip and is pulled out from the circular stapler in one piece via the guide hole, which is similar to the case of pulling the "spring wire" into a straight wire. In this process, as the second flexible strip 64 has lower strength it can be easily pulled apart, and broken bodies of the second flexible strip 64 together with the first flexible strip 63 can be pulled out from the circular stapler. Certainly, the above embodiment may also be changed to be pulled out from the outside of the stapler as long as the connecting position of the traction member on the introducer accessory is changed.

Figure 14:
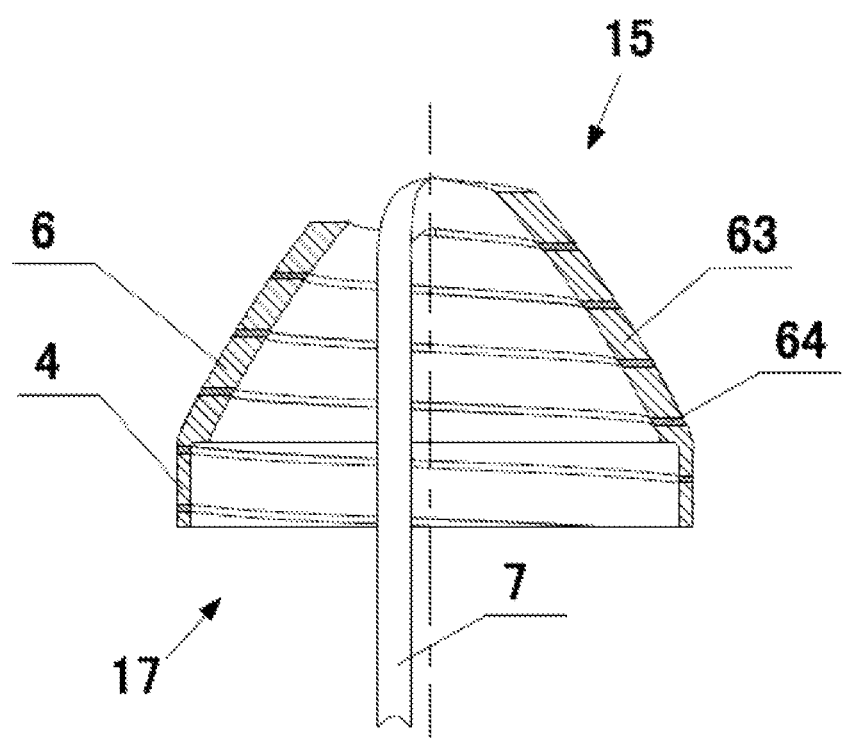
FIG. 14 is a schematic structural view of a sixth embodiment of the present disclosure.
Figure 15:
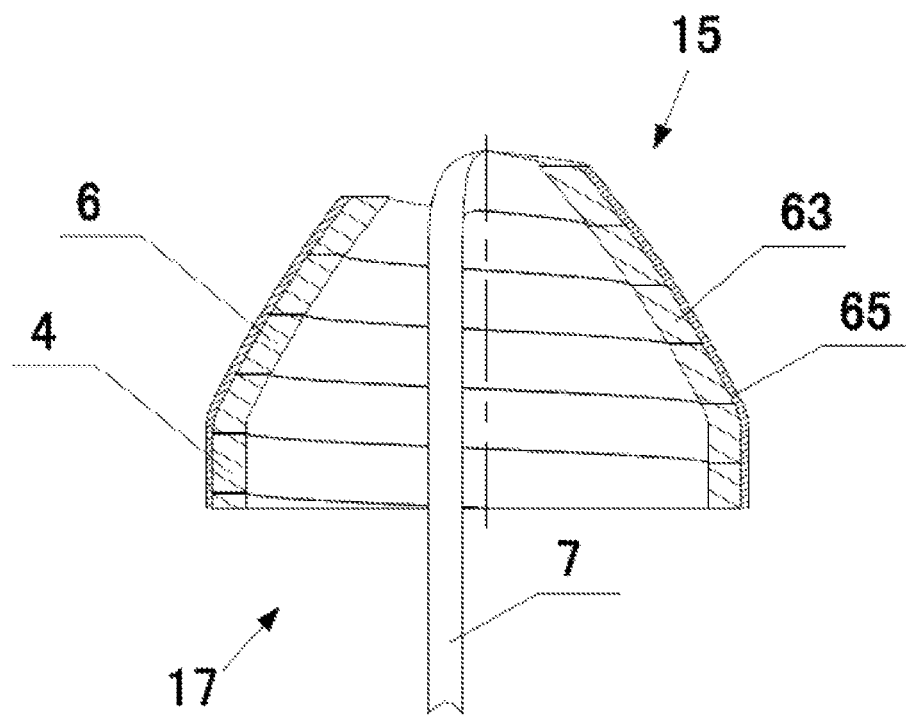
FIG. 15 is a schematic structural view of a seventh embodiment of the present disclosure.
Figure 16:
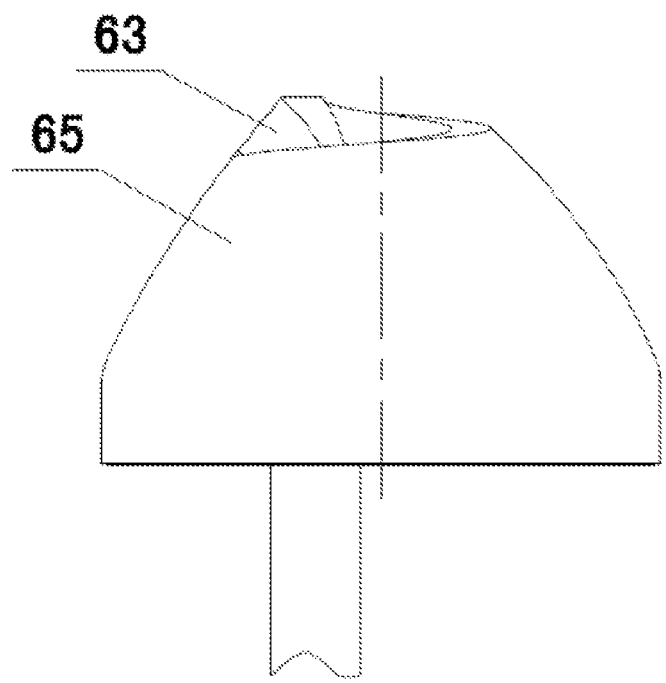
FIG. 16 is a front view of the seventh embodiment of the present disclosure.
Figure 17:
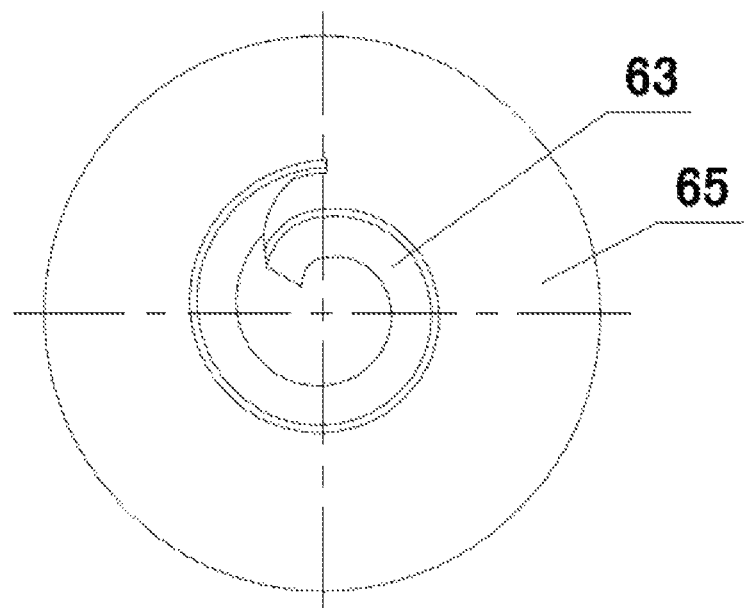
FIG. 17 is a top view of the seventh embodiment of the present disclosure.

FIG. 14 illustrates the sixth embodiment of the present disclosure. When the wall thickness of the sleeve portion 4 is relatively large, the whole outer diameter of the circular stapler with the introducer accessory is obviously increased, and hence the insertion of the circular stapler would be influenced and the pain of a patient would be aggravated as well. Therefore, in the sixth embodiment, the wall thickness of the sleeve portion 4 is less than that of the introducing portion 6, and hence the influence due to the wall thickness can be greatly reduced. Other structures and the operation method of the sixth embodiment are the same as those of the fifth embodiment and hence will not be further described herein.

FIGS. 15 to 18 illustrate the seventh embodiment of the present disclosure. The characteristics of the embodiment are that: the conical wall of the introducer includes an inner layer and an outer layer; the inner first layer is a spiral body formed by the winding of first flexible strip 63; and the outer second layer is a second membrane layer 65 covering on the outside of the first layer. Certainly, the case that the spiral body formed by the winding of the first flexible strip 63 is disposed outside and the second membrane layer 65 covering on the inside of the first layer is disposed inside is not excluded from the scope of the present disclosure.

Figure 20:
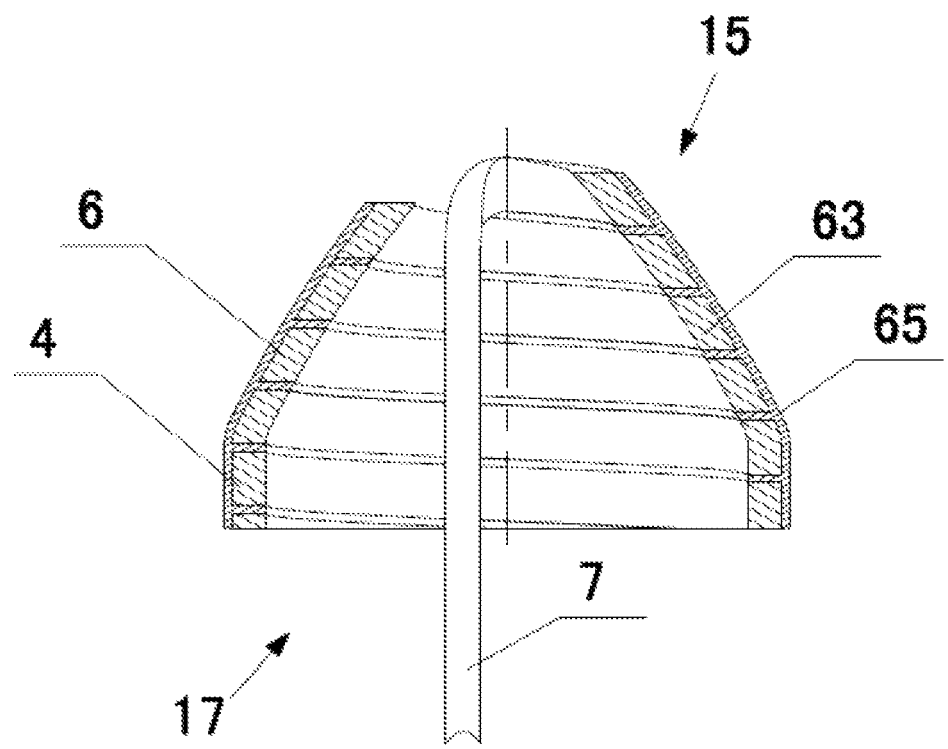
FIG. 20 is a schematic structural view of a ninth embodiment of the present disclosure.
Figure 21:
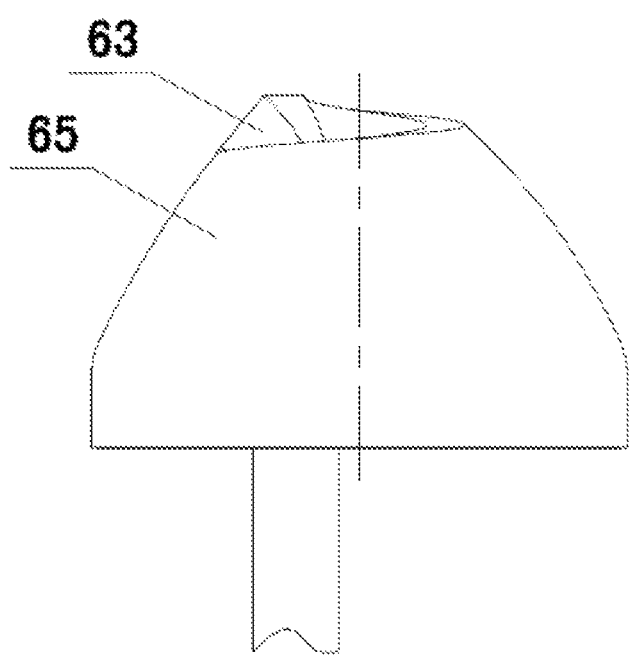
FIG. 21 is a front view of the ninth embodiment of the present disclosure.
Figure 22:
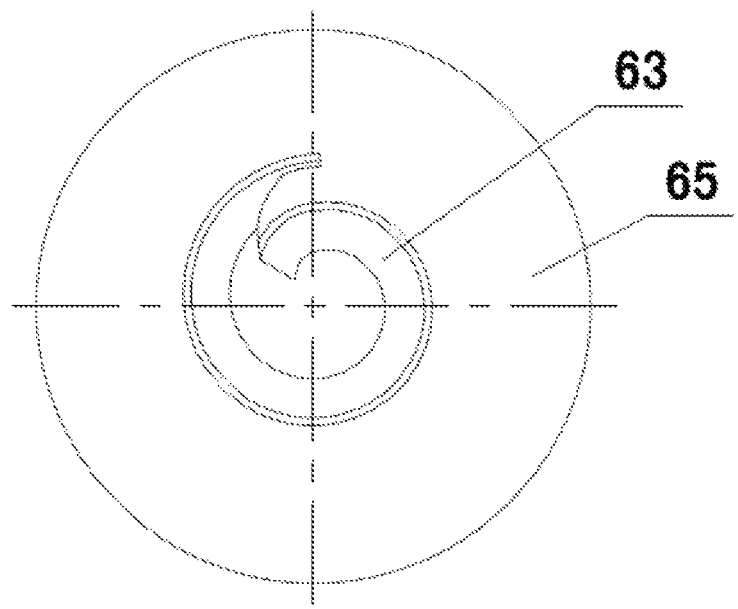
FIG. 22 is a top view of the ninth embodiment of the present disclosure.

In the embodiment, the first flexible strip 63 is tightly and spirally arranged, and the second membrane layer 65 is only covering on the outside of the conical wall 51. In the ninth embodiment as illustrated in FIGS. 20 to 22, the first flexible strip 63 is spirally arranged, the second membrane layer 65 is covering on the outside of the conical wall 51, and partial second membrane layer 65 is extended into between spiral wires of the first flexible strip 63, so that the first flexible strip 63 and the second membrane layer 65 are attached with each other and arranged alternately and spirally.

The first flexible strip 63 is made of relatively rigid materials, thereby with higher strength and higher hardness; and the second membrane layer 65 is made of relatively soil material, thereby with lower strength and being easily torn. Moreover, the first flexible strip 63 and the second membrane layer 65 are mutually attached by bonding or over-molding.

In the seventh embodiment and the ninth embodiment, the sleeve portion 4 is the extension of the first flexible strip and the first flexible strip of the sleeve portion 4 is integrally formed with the first flexible strip 63 of the introducing portion 6. The second membrane layer 65 is coated on the outside of the first flexible strip of the sleeve portion and the introducing portion.

A traction member 7 is also disposed at the distal end of the first flexible strip 63. The traction member 7 is an extension of a distal end of the first flexible strip 63, and a free end of the traction member 7 is extended toward the proximal end of the circular stapler. Alternatively, the traction member 7 may also be a traction string fixed at the distal end of the first flexible strip 63 as long as the pulling function can be achieved. Moreover, at least one guide hole is formed on the staple cylinder of the circular stapler, and the traction member 7 in the initial state runs through the guide hole.

As the first flexible strip 63 are tightly wound in the seventh embodiment and the first flexible strip 63 and partial second membrane layer 65 are tightly wound in the ninth embodiment, the conical wall of the whole introducing portion has relative high strength and hence cannot be collapsed when the circular stapler is introduced into the body of a patient. Moreover, as the second membrane layer 65 is integrally coated on the outside of the first flexible strips 63, the outside of the conical wall 51 of the whole introducer accessory is relatively smooth, so that the outer wall cannot scratch the tissue when the circular stapler is introduced into the body of the patient, and thereby with much better effect than that of single spiral flexible strip.

The operation method of the seventh embodiment is identical with that of the ninth embodiment. Description will be given below by taking the seventh embodiment as an example.

Figure 18:
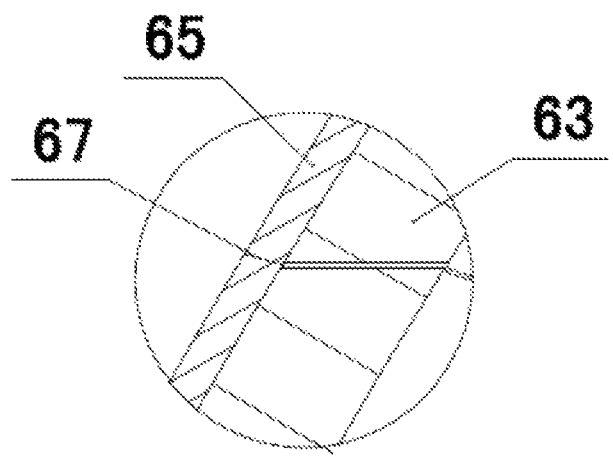
FIG. 18 is a partial enlarged view illustrating the state when the seventh embodiment of the present disclosure is torn.

In the operation process, firstly, the introducer accessory of the preferred embodiment is sleeved around a distal end of the staple cartridge assembly; then, the circular stapler is introduced into the human body, and at this moment, the free end of the traction member 7 runs through the guide hole and is exposed out of the body of a patient; and next, the traction member 7 is pulled so that the second membrane layer 65 together with the first flexible strip 63 can be unwound spirally in the sequence from distal to proximal and finally forms a strip body which is pulled out from the circular stapler in one piece via the guide hole, which is similar to the state of pulling the "spring wire" into a straight wire. In the process, as the second membrane layer 65 has relative low strength and hence is easily pulled apart, so that a tear line 67 of the second membrane layer 65 as illustrated in FIG. 18 occurs near two adjacent spiral wires of the wound first flexible strip 63, and a broken body of the second membrane layer 65 can be pulled out from the circular stapler together with the first flexible strip 63. Certainly, the above embodiment may also be changed to be pulled out from the outside of the stapler as long as the connecting position of the traction member on the introducer accessory is changed.

Figure 19:
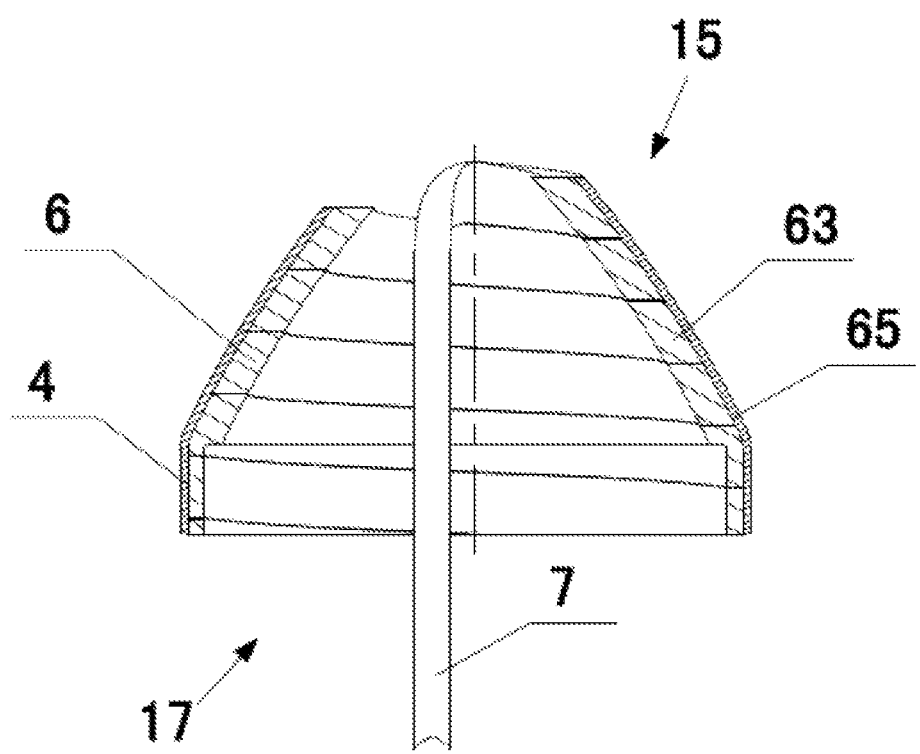
FIG. 19 is a schematic structural view of an eighth embodiment of the present disclosure.

FIG. 19 illustrates the eighth embodiment of the present disclosure. The difference of the embodiment with the seventh embodiment is that: the wall thickness of the sleeve portion 4 is less than that of the introducing portion 6. Therefore, the influence due to the wall thickness can be greatly reduced. Other structures and the operation method of the eighth embodiment are the same as those of the seventh embodiment and will not be further described herein.

Figure 23:
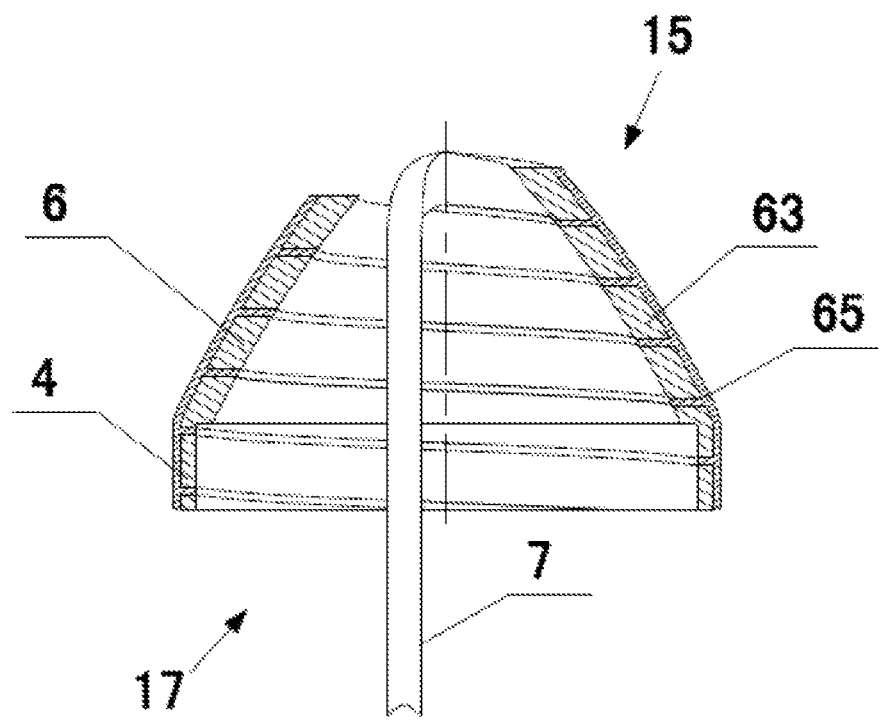
FIG. 23 is a schematic structural view of a tenth embodiment of the present disclosure.

FIG. 23 illustrates the tenth embodiment of the present disclosure. The difference of the embodiment with the ninth embodiment is that: the wall thickness of the sleeve portion is less than that of the introducing portion 6. Therefore, the influence due to the wall thickness can be greatly reduced. Other structures and the operation method of the tenth embodiment are the same with those of the ninth embodiment and will not be further described herein.

As similar to the first embodiment, in the above embodiments, a chromatic area, particularly in yellow, for being distinguished with the whole introducer accessory, is formed at the proximal end of the introducer accessory, generally by spraying method. The chromatic area is used for indicating the doctor that the whole introducer accessory has been completely removed out of the circular stapler. Due to the yellow area, when the surgeon sees the yellow area, it is indicated that the introducer accessory has been completely pulled out from the circular stapler.

The introducer accessory in the present disclosure has simple operation and the introducer accessory can be disengaged from the circular stapler in one step. However, in the related art, the process requires multi-step operation, and the spring wires of the introducer accessory cannot be released in the form of a strip and hence can easily scratch the tissue.

The introducer accessory in the present disclosure may also have a plurality of embodiments. All the technical proposals formed by equivalent replacements or variations to the disclosed embodiments should fall within the scope of protection of the present disclosure.

What is claimed is:

1. An introducer accessory for being fitted with a circular stapler, the circular stapler comprising an anvil assembly and a staple cartridge assembly, the staple cartridge assembly including a staple cylinder and a staple cartridge being mutually fixed and a trocar disposed in the staple cartridge, a proximal end of the staple cylinder being provided with at least one through hole; wherein
   the introducer accessory at least comprises a sleeve portion sleeved around a distal end of the circular stapler and an introducing portion disposed at a distal end of the sleeve portion; a maximum outer diameter of the introducing portion is equal to a minimum outer diameter of the sleeve portion;
   the introducing portion comprises a flexible plastic spiral member and a traction member; the flexible plastic spiral member is in a conical shape with a cavity and has a distal end and a proximal end, outer diameter of the flexible plastic spiral member is gradually increased from the distal end to the proximal end; the proximal end of the flexible plastic spiral member is connected with the sleeve portion; and the traction member extends in the cavity of spiral member to connect with the distal end of the flexible plastic spiral member such that when the traction member is pulled by an external force, the distal end of the flexible plastic spiral member is pulled inward by the traction member and through the cavity which causes the flexible plastic spiral member to be unwound internally and spirally in a sequence from distal to proximal and finally to form a strip body to withdraw from the circular stapler via the through hole.

2. The introducer accessory according to claim 1, wherein the sleeve portion is in a shape of a cylinder or a semicircular cylinder; and inner diameter of the sleeve portion is greater than outer diameter of the staple cylinder.

3. The introducer accessory according to claim 1, further comprising a flange for holding, which is disposed at a proximal end of the sleeve portion and configured to be spread out.

4. The introducer accessory according to claim 1, wherein a group of reinforcing ribs are perpendicularly disposed between adjacent spiral passes of the flexible plastic spiral member respectively.

5. The introducer accessory according to claim 1, wherein one end of the traction member is connected to a furthermost center of the spiral wires.

6. The introducer accessory according to claim 5, wherein the traction member runs through the through hole of the staple cylinder, and a pull ring is disposed at the other end of the traction member.

7. The introducer accessory according to claim 1, wherein the flexible plastic spiral member is configured to be consisted of two spiral wires which are alternately wound; first ends of the two spiral wires are connected with each other and second ends of the two spiral wires are connected with the sleeve portion.

8. The introducer accessory according to claim 7, wherein the traction member is hooked on a connected end portion of the two spiral wires.

9. The introducer accessory according to claim 1, wherein the sleeve portion is a thin wall sleeved around periphery of the staple cartridge; and the introducing portion and the sleeve portion are combined to form a spiral flexible plastic member formed by integral injection molding.

10. The introducer accessory according to claim 9, wherein a central tube with inner diameter equal to outer diameter of a distal end of the trocar is protruded inwards from bottom of a distal end of a hollow inner cavity of the introducing portion.

11. The introducer accessory according to claim 10, wherein a traction hole is formed on a wall at a proximal end of the central tube which is one end of the whole flexible plastic spiral member.

12. The introducer accessory according to claim 1, wherein a conical wall of the introducing portion includes a flexible strip and a second flexible strip which are attached tightly and arranged alternately and spirally; and when pulled by an external force, the conical wall is unwound spirally in a sequence from distal to proximal and finally forms a strip body which consists of the first flexible strip and the second flexible strip and can be disengaged from the circular stapler via the through hole.

13. The introducer accessory according to claim 12, wherein the sleeve portion includes a first flexible strip and a second flexible strip which are attached tightly and arranged alternately and spirally; and the first flexible strip and the second flexible strip of the sleeve portion are respectively integrally formed with the first flexible strip and the second flexible strip of the introducing portion.

14. The introducer accessory according to claim 12, wherein wall thickness of the sleeve portion is less than that of the introducing portion.

15. The introducer accessory according to claim 12, wherein the first flexible strip is made of rigid material; the second flexible strip is made of soft materials; and the first flexible strip and the second flexible strip are mutually attached by bonding or over-molding.

16. The introducer accessory according to claim 12, wherein a traction member is disposed at a distal end of the first flexible strip.

17. The introducer accessory according to claim 16, wherein the traction member is an extension of the distal end of the first flexible strip, a free end of the traction member is extended to a proximal end of the circular stapler; or the traction member is a traction string fixed at the distal end of the first flexible strip.

18. The introducer accessory according to claim 1, wherein a conical wall of the introducing portion includes an inner layer and an outer layer, wherein a first layer is a spiral body formed by the winding of a first flexible strip and a second layer is a second membrane layer covering on the first layer such that when pulled by an external force, the second membrane layer together with the first flexible strip are unwound spirally in a sequence from distal to proximal and finally forms a strip body capable of being disengaged from the circular stapler via the through hole.

19. The introducer accessory according to claim 18, wherein the first flexible strip is tightly and spirally arranged; and the second membrane layer is only covering on outside or inside of the conical wall.

20. The introducer accessory according to claim 18, wherein the first flexible strip is spirally arranged; the second membrane layer is covering on outside or inside of the conical wall, and partial second membrane layer is extended into between spiral wires of the first flexible strip so that the first flexible strip and the second membrane layer can be attached tightly and arranged alternately and spirally.

21. The introducer accessory according to 18, wherein the sleeve portion is configured to one part of the first flexible strip; and the first flexible strip of the sleeve portion and the first flexible strip of the introducing portion are integrally formed.

22. The introducer accessory according to claim 21, wherein the second membrane layer is covering on outside of the first flexible strips of the sleeve portion and the introducing portion.

23. The introducer accessory according to claim 22, wherein wall thickness of the sleeve portion is less than that of the introducing portion.

24. The introducer accessory according to claim 21, wherein the first flexible strip is made of rigid material; the second membrane layer is made of soft material; and the first flexible strips and the second membrane layer are mutually attached by bonding or over-molding.

25. The introducer accessory according to claim 21, wherein a traction member is disposed at distal end of the first flexible strip.

26. The introducer accessory according to claim 25, wherein the traction member is an extension of the distal end of the first flexible strip, a free end of the traction member is extended toward a proximal end of the circular stapler; or, the traction member is a traction string fixed at the distal end of the first flexible strip.

27. An introducer accessory for being fitted with a circular stapler, the circular stapler comprising an anvil assembly and a staple cartridge assembly, the staple cartridge assembly including a staple cylinder and a staple cartridge being mutually fixed, wherein
the introducer accessory at least comprises a sleeve portion sleeved around a distal end of the circular stapler and an introducing portion disposed at a distal end of the sleeve portion; a maximum outer diameter of the introducing portion is equal to a minimum outer diameter of the sleeve portion;
the introducing portion comprises a flexible U-shaped circuitous member with a U-shaped central cross-section formed by integral injection molding and a traction member; the U-shaped circuitous member has a proximal end and a distal end; and outer diameter of the distal end is less than or equal to outer diameter of the proximal end;
the U-shaped circuitous member has a cavity inside and the traction member extends in the cavity to connect with the distal end of the U-shaped circuitous member such that when the traction member is pulled by an external force, the distal end of the U-shaped circuitous member is pulled inward by the traction member and through the cavity which causes the U-shaped circuitous member to be unwound internally and withdraw from the circular stapler.

28. The introducer accessory according to claim 27, wherein the sleeve portion is a thin wall sleeved around periphery of the staple cartridge.

29. The introducer accessory according to claim 28, wherein a clamp fixedly connected to the staple cartridge is disposed on the thin wall.

* * * * *